US009659744B2

(12) United States Patent
Tsuno et al.

(10) Patent No.: US 9,659,744 B2
(45) Date of Patent: May 23, 2017

(54) CHARGED PARTICLE BEAM APPARATUS AND INSPECTION METHOD USING THE SAME

(71) Applicant: HITACHI HIGH-TECHNOLOGIES CORPORATION, Minato-ku, Tokyo (JP)

(72) Inventors: Natsuki Tsuno, Tokyo (JP); Naomasa Suzuki, Tokyo (JP); Hideyuki Kazumi, Tokyo (JP); Shoji Hotta, Tokyo (JP); Yoshinobu Kimura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/948,167

(22) Filed: Nov. 20, 2015

(65) Prior Publication Data
US 2016/0148781 A1    May 26, 2016

(30) Foreign Application Priority Data

Nov. 20, 2014    (JP) .................................. 2014-235578

(51) Int. Cl.
| | |
|---|---|
| H01J 37/28 | (2006.01) |
| G01B 15/04 | (2006.01) |
| H01J 37/244 | (2006.01) |
| G01N 23/00 | (2006.01) |

(52) U.S. Cl.
CPC ............ H01J 37/244 (2013.01); G01N 23/00 (2013.01); H01J 37/28 (2013.01); *H01J 2237/24592* (2013.01)

(58) Field of Classification Search
CPC ........ H01J 37/28; H01J 37/222; H01J 37/263; H01J 37/265; H01J 37/244; H01J 37/285; G01B 15/04; G01B 23/22

USPC ................................. 250/310, 307, 306, 311
See application file for complete search history.

(56) References Cited

U.S. PATENT DOCUMENTS

| | | | | | |
|---|---|---|---|---|---|
| 5,260,648 | A | * | 11/1993 | Brust | .................... G01R 31/305 250/311 |
| 7,943,533 | B2 | * | 5/2011 | Mizuno | ............... H01L 21/0268 438/166 |
| 8,673,428 | B2 | * | 3/2014 | Naoyuki | ................... B41C 1/00 428/167 |

(Continued)

FOREIGN PATENT DOCUMENTS

JP    2012-252913 A    12/2012

*Primary Examiner* — David A Vanore
(74) *Attorney, Agent, or Firm* — Miles & Stockbridge P.C.

(57) ABSTRACT

A charged particle beam apparatus makes it possible to acquire information in the cross-sectional direction (depth direction) of a sample having an internal structure in a nondestructive manner with reduced damage. Further, the apparatus makes it possible to analyze the depth and/or dimensions in the depth direction of the internal structure. The charged particle beam apparatus includes: a means for providing a time base for control signals; a means for applying a charged particle beam to a sample in synchronization with the time base and controlling an irradiation position; a means for analyzing the emission characteristics of an emission electron from the sample from a detection signal of the emission electron; and a means for analyzing the electrical characteristics or cross-sectional morphological characteristics of the sample based on the emission characteristics.

13 Claims, 13 Drawing Sheets

(56) References Cited

U.S. PATENT DOCUMENTS

| | | | |
|---|---|---|---|
| 8,841,612 B2* | 9/2014 | Fukuda | H01J 37/222 250/306 |
| 8,907,279 B2* | 12/2014 | Tsuno | H01J 37/28 250/307 |
| 2013/0126733 A1* | 5/2013 | Fukuda | H01J 37/222 250/310 |
| 2014/0097342 A1* | 4/2014 | Tsuno | H01J 37/28 250/307 |
| 2016/0148781 A1* | 5/2016 | Tsuno | H01J 37/244 250/307 |

* cited by examiner

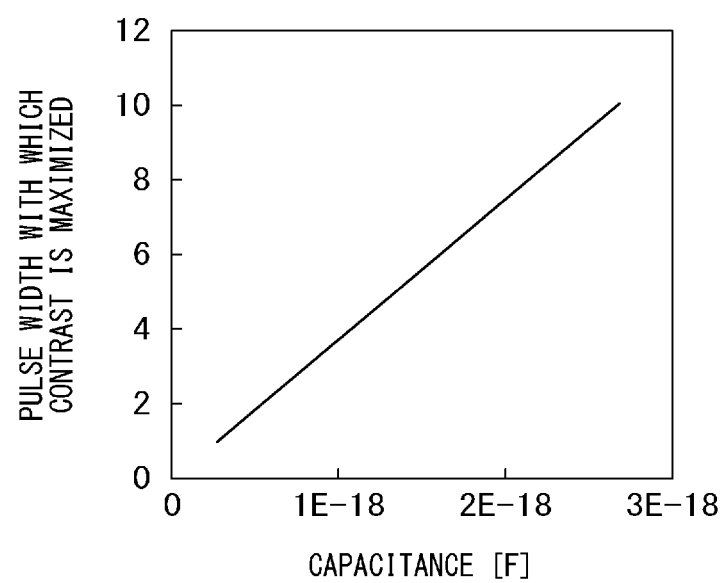
F I G . 1 4

CHARGED PARTICLE BEAM APPARATUS AND INSPECTION METHOD USING THE SAME

CLAIM OF PRIORITY

The present application claims priority from Japanese patent application JP 2014-235578 filed on Nov. 20, 2014, the content of which is hereby incorporated by reference into this application.

TECHNICAL FIELD

The present invention relates to a charged particle beam apparatus and an inspection method using the same.

BACKGROUND ART

Among charged particle beam apparatuses, there are electron microscopes as microscopes with which a sample can be magnified and observed. Electron microscopes use an electron beam and are utilized in micro-shape observation and composition analysis at the nanometer level. Especially, scanning electron microscopes (hereafter, abbreviated as SEMs) are characterized in that SEMs enables analysis dimensions of the order from millimeters to nanometers without being limited by sample sizes and in wide use from morphological and compositional analysis of high-performance materials to measurements and inspections on fine patterns of semiconductor devices. In these morphological and compositional analysis and fine pattern measurements and inspections, generally, it is required to analyze not only information of the surfaces of samples but also information in the cross-sectional direction (depth direction) such as the materials and structures of the interior of samples. To acquire information in the cross-sectional direction, generally, a sample is cut open and the resulting section is observed; however, this is destructive observation. In some SEM methods of analyzing the interior of a sample in a nondestructive manner, the acceleration voltage of an electron beam applied to an electron source is controlled. In SEMs, the energy of an electron beam applied to a sample is adjusted by controlling acceleration voltage. The depth to which an electron beam penetrates a sample depends on the energy of the electron beam and reflection electrons are emitted from an internal structure located in the depth position to which the electron beam penetrates. A SEM image mainly embracing information of the interior of the sample is obtained by detecting the reflection electrons. Japanese Unexamined Patent Application Publication No. 2012-252913 discloses a method in which the amount of irradiation of electrons is controlled by a pulsed electron beam and embedded structures are observed by voltage contrast arising from surface electrification. The voltage contrast reflects a difference in surface potential produced by electrification by electron beam irradiation. The difference in surface potential is caused by a difference in electrical characteristics (resistance and capacitance) from sample to sample. Since the electrical characteristics of samples differ depending on the presence or absence of an internal structure of each sample, the internal structure can be visualized by voltage contrast with controlled electrification.

SUMMARY OF THE INVENTION

Sample information obtained by SEM images with controlled acceleration voltage or voltage contrast images by a pulsed electron beam described in Japanese Unexamined Patent Application Publication No. 2012-252913 are mainly as follows: the presence or absence of an internal structure and the lateral size of an internal structure. The information does not include the depth at which an internal structure is located (how deeply an internal structure exists) or the length in the cross-sectional direction (dimensions in the depth direction). To cope with this, the inventors considered a method for analyzing information in the cross-sectional direction. In the method, acceleration voltage is variably controlled; the penetration depth of an electron beam is calculated from an acceleration voltage value with which an internal structure can be identified; and the information of the sample in the cross-sectional direction is thereby estimated. However, this method involves a problem. Since an electron beam penetrates a sample with random motion due to scattering, the penetration depth varies. For this reason, the above method is inferior in the accuracy of sample analysis in the cross-sectional direction and it has been found that since an electron beam is caused to penetrate to the interior, damage to the sample is not negligible.

It is an object of the present invention to provide a charged particle beam apparatus and an inspection method using the same in which the above problem is solved. With the apparatus and the method, information in the cross-sectional direction (depth direction) of a sample having an internal structure is acquired in a nondestructive manner with reduced damage; and the electrical characteristics or the morphological characteristics (the depth and/or dimensions in the depth direction of the internal structure and the like) in the cross-sectional direction of the sample are analyzed.

According to an embodiment for achieving the above object, a charged particle beam apparatus includes:

a charged particle beam source;

a means for setting the irradiation energy of a charged particle beam emitted from the charged particle source;

a means for providing a time base for control signals;

a means for applying the charged particle beam to a sample in synchronization with the time base and controlling an irradiation position;

a means for detecting emission electrons from the sample in synchronization with the time base;

a means for analyzing the emission characteristics of the emission electrons from a detection signal of the emission electrons; and a means for analyzing the electrical characteristics or cross-sectional morphological characteristics of the sample based on the emission characteristics of the emission electrons.

According to an embodiment for achieving the above object, a charged particle beam apparatus includes:

a charged particle beam source;

a means for setting the irradiation energy of a charged particle beam emitted from the charged particle source;

a means for providing a time base for control signals;

a means for applying the charged particle beam to a sample in synchronization with the time base and controlling an irradiation position;

a means for detecting emission electrons from the sample in synchronization with the time base;

a means for forming an image from a first control signal for controlling the irradiation position, a second control signal for applying the charged particle beam to the sample, and a detection signal of the emission electrons; and a means for analyzing the electrical characteristics or cross-sectional morphological characteristics of the sample from the brightness or contrast of the image.

According to an embodiment for achieving the above object, an inspection method includes:

a step of preparing a test sample in which a conductive layer is covered with an insulating layer;

a step of irradiating a region of interest of the test sample where the conductive layer is formed with charged particle beams different in pulse width through the insulating layer to obtain a plurality of images different in contrast;

a step of extracting a pulse width with which contrast is maximized from the images;

a step of extracting capacitance corresponding to a pulse width with which contrast is maximized in the region of interest of the test sample using relation between pulse width with which contrast is maximized and capacitance, obtained using a standard sample in which an insulating layer having a known thickness is so formed as to cover a conductive layer;

a step of obtaining the depth position of the conductive layer of the test sample using the extracted capacitance; and a step of comparing the obtained depth position of the conductive layer with a predetermined criterion to determine whether the test sample is non-defective or defective.

According to the claimed invention, it is possible to provide a charged particle beam apparatus and an inspection method using the same in which: information in the cross-sectional direction (depth direction) of a sample having an internal structure is acquired in a nondestructive manner with reduced damage; and the depth and/or dimensions in the depth direction of the internal structure are analyzed.

BRIEF DESCRIPTION OF THE DRAWINGS

FIG. 14 is a drawing showing an example of calibration data (relation between pulse width with which contrast is maximized and capacitance) used in an inspection method in the third embodiment of the present invention;

DESCRIPTION OF THE PREFERRED EMBODIMENTS

Figure 1:
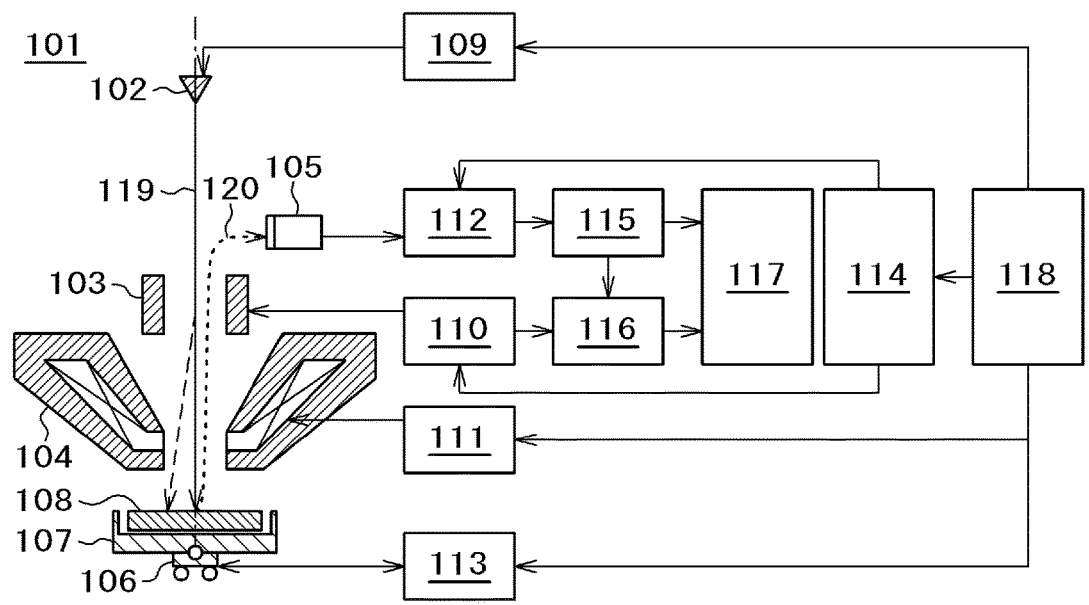
FIG. 1 is a block diagram illustrating an example of a charged particle beam apparatus (scanning electron microscope) in a first embodiment of the present invention.

The inventors considered various methods for acquiring the information in the cross-sectional direction (depth direction) of a sample having an internal structure in a nondestructive manner with reduced damage and noted capacitance including information of distance. Hereafter, a description will be given to the result of this consideration made from this point of view.

When the sample is an insulator, the surface of the sample is electrified by irradiation of an electron beam. Letting the secondary electron emission rate o be the ratio of the amount of secondary electron emission to the amount of electron irradiation, the secondary electron emission rate o changes with time by electrification by electron beam irradiation. The amount of electric charge Q accumulated in the sample at this time is expressed by Equation (1):

$$Q=(\sigma_i-1)\int_{t=0}^{\infty}e^{(-t/\tau)}dt \qquad (1)$$

where, $\sigma_i$ is the true secondary electron emission rate intrinsic to the material not influenced by electrification; t is electron irradiation time; and $\tau$ is the time constant of time change in the secondary electron emission rate due to electrification. The capacitance C of the sample is as expressed by Equation (2):

$$C=Q/V \qquad (2)$$

where, V is the surface potential of the sample. From Equation (1) and Equation (2), the capacitance C is a function of the true secondary electron emission rate $\sigma_i$ and the time constant $\tau$ of time change in the secondary electron emission rate. It is understood that the capacitance C in the irradiation position of the electron beam can be calculated based on the analysis of $\sigma_i$ and $\tau$ of the sample. The capacitance C is expressed by Equation (3):

$$C=\epsilon \cdot S/d \qquad (3)$$

where, ϵ is the permittivity of the material; S is the irradiation area of the electron beam; and d is the thickness of the material. Therefore, from the calculated capacitance, the thickness of the sample can be analyzed based on Equation (3). The laminar structure of a laminated sample can also be analyzed in accordance with a synthetic capacitance model obtained by expanding Equation (3). In this method, it is unnecessary to let an electron beam penetrate into the interior and as low an acceleration voltage as 5 kV or below, suitable for electrification control, is used. This makes it possible to suppress sample damage due to electron beam irradiation.

The claimed invention has been made based on findings about the above-mentioned transient characteristics of secondary electron emission rate. An electron microscope capable of analyzing sample information in the cross-sectional direction (depth direction) according to the present invention includes: an irradiating means for electron beams with a time base established; a detecting means for secondary electrons in synchronization with the time base; and a means for analyzing the electrical characteristics of a sample or the information in the cross-sectional direction of the sample from the transient characteristics (emission characteristics) of a detection signal of the secondary electron acquired by the detecting means. With this method, the information in the cross-sectional direction of a sample can be accurately analyzed in a nondestructive manner.

The transient characteristics (emission characteristics) of the detection signal of the secondary electron cited here is any of the signal value of the detection signal, a time constant with which the signal value is brought into a steady state, and an integrated value of the signal value.

The contrast CNR of a SEM image is the difference in secondary electron emission rate between region A and region B and in case of an electrification sample in which the secondary electron emission rate changes with time, the contrast is as expressed by Equation (4):

$$CNR = (\sigma_{i_A} - 1)e^{(-t/\tau_A)} - (\sigma_{i_B} - 1)e^{(-t/\tau_B)} \quad (4)$$

where, t is the electron irradiation time per unit area (pixel size, the scanning distance of an electron beam, visual field size). Similarly to Equation (1), the time quadrature of Equation (4) is the difference in the amount of electric charges Q accumulated in regions A and B. It is understood from Equation (2) that the difference in the amount of accumulated electric charges Q is equivalent to a difference in capacitance. That is, a difference in capacitance can be estimated from the contrast of a SEM image acquired by controlling the electron irradiation time per unit area (pixel size, the scanning distance of an electron beam, visual field size).

An electron microscope according to the present invention capable of sample information in the cross-sectional direction (depth direction) includes: an irradiating means for an electron beam with a time base established; a deflecting means for the electron beam in synchronization with the time base; a detecting means for secondary electrons in synchronization with the time base; a means for forming a SEM image from a detection signal of the secondary electrons acquired by the detecting means; and a means for analyzing the electrical characteristics of a sample or the information in the cross-sectional direction of the sample from the brightness and contrast of the SEM image.

Since the time quadrature of Equation (4) is the difference in capacitance in regions A and B, the thickness and the information of a laminar structure of a sample can be extracted by taking the following procedure: the difference in capacitance is calculated from a cumulative value of the contrast of a SEM image acquired with a plurality of electron irradiation times t; and Equation (3) is used. The brightness and contrast of the SEM image are the brightness and contrast of a plurality of the SEM images acquired under a plurality of electron irradiation conditions.

The irradiating means for an electron beam with the time base established is a means for intermittently applying an electron beam in synchronization with the time base.

The means for intermittently applying an electron beam in synchronization with the time base is a means for controlling an electron irradiation time and time intervals between intermittent irradiations.

The electrical characteristics or information in the cross-sectional direction of the sample is characterized in that: the electrical characteristics are the capacitance or resistance value of the sample; and the information in the cross-sectional direction is the depth position, length, and thickness of a lower layer structure.

The above electron microscope includes a means for holding a database and a means for analyzing information based on the database. The database indicates the relation between the transient characteristics (emission characteristics) of the detection signal of secondary electrons or the brightness and contrast of the SEM image and the electrical characteristics or the information in the cross-sectional direction. The analyzing means analyzes the electrical characteristics or the information in the cross-sectional direction from the transient characteristics of the detection signal of secondary electrons or the brightness and contrast of the SEM image.

The above electron microscope includes a means for analyzing the electrical characteristics or information in the cross-sectional direction of the sample in a plurality of places in the sample. The means then displays a mapping image of the electrical characteristics or information in the cross-sectional direction of the sample.

The sample is a wafer in a manufacturing process for semiconductor devices. The above electron microscope includes a means for analyzing the dimensions of a fine pattern formed in the wafer or malformation of the fine pattern.

The means for analyzing the malformation of a fine pattern extracts a defective point in a fine pattern formed in the wafer from a difference in the brightness or contrast of an image formed under single irradiation conditions. The electrical characteristics or cross-sectional morphological characteristics of the sample are analyzed based on the brightness or contrast of the image analyzed from a plurality of images acquired at the extracted defective point under a plurality of irradiation conditions.

Hereafter, a description will be given to the present invention based on embodiments with reference to the drawings. The identical reference numerals denote identical componential elements. In the following description of the embodiments, a scanning electron microscope using electron as primary charged particle is taken as an example; however, the present invention is also applicable to apparatuses using ion as primary charged particle.

First Embodiment

A description will be given to the first embodiment of the present invention with reference to FIG. 1 to FIG. 6. In the following description of this embodiment, a scanning electron microscope will be taken as an example of a charged particle beam apparatus. In the charged particle beam apparatus, information in the cross-sectional direction is analyzed based on the transient characteristics (emission characteristics) of a detection signal of secondary electrons. FIG. 1 is a block diagram of the scanning electron microscope in this embodiment. The scanning electron microscope 101 is made up of an electronic optical system, a stage mechanism system, a control system, an image processing system, and an operating system. The electronic optical system is made up of an electron gun 102, a deflector 103, an objective lens 104, and a detector 105. The stage mechanism system is made up of an XYZ stage 106 and a sample holder 107. To the sample holder 107, a voltage applying means may be connected for applying voltage to a sample 108. The control system is made up of: an electron gun control unit 109, a deflection signal control unit 110, an objective lens coil control unit 111, a detector control unit 112, an XYZ stage control unit 113, and a master clock generation unit 114 which time synchronizes the deflection signal control unit 110 with the detector control unit 112. The image processing system is made up of a detection signal processing unit 115 and an image formation unit 116. The operating system is made up of: an analysis and display unit 117 including a display portion for displaying the result of analysis by the detection signal processing unit 115 and the image formation unit 116; and a control parameter setting unit 118 for the control system including an operating interface. An electron beam 119 accelerated by the electron gun 102 is focused through the objective lens 104 and is applied to the sample 108. An irradiation position on the sample is controlled by the deflector 103. Secondary electrons 120 emitted from the sample 108 are influenced by the electric field on the sample and induced and detected by the detector 105. When the transient characteristics of a detection signal of the secondary electrons 120 are analyzed, the electron beam 119 is set out of an analysis region using the deflector 103. The electron beam is moved to outside the analysis region through the deflector 103 by the deflection signal control unit 110 with timing controlled by the master clock generation unit 114. At the same time, a detection signal of the secondary electrons 120 emitted from the sample 108 is sampled at the detector control unit 112. Then the transient characteristics of the detection signal of the secondary electrons are analyzed at the detection signal processing unit 115.

Figure 2:
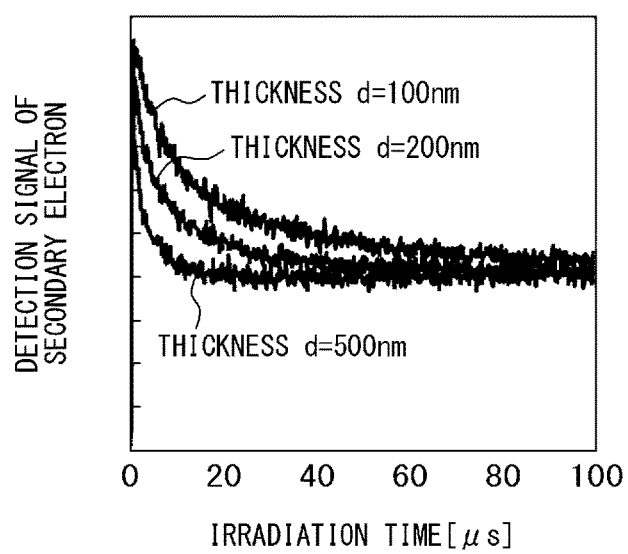
FIG. 2 is a drawing showing the irradiation time dependence of a detection signal of a secondary electron obtained with a scanning electron microscope in the first embodiment of the present invention.

FIG. 2 shows the irradiation time dependence of detection signals of secondary electrons of samples different in oxide film thickness d acquired at acceleration voltage of 300V and irradiation current of 10 pA. With respect to acceleration voltage, it is desirable from the viewpoint of aberration reduction that: voltage of 300V or above should be applied to accelerate the electron beam, which is thereafter decelerated and when the electron beam is applied to the sample, acceleration voltage of 300V should be obtained. In this embodiment, oxide films of the same type are used, the true secondary electron emission rate $\sigma_t$ not influenced by electrification is constant regardless of film thickness. Therefore, also for the detection signal of secondary electrons immediately after irradiation, the detection signal is constant regardless of film thickness. However, the irradiation time dependence when the detection signal of secondary electrons is brought into a steady state becomes steeper with increase in oxide film thickness d. From the irradiation time dependence of the detection signal of secondary electrons shown in FIG. 2, the time constant with which the detection signal of secondary electrons is brought into a steady state is analyzed by the detection signal processing unit 115.

Figure 3:
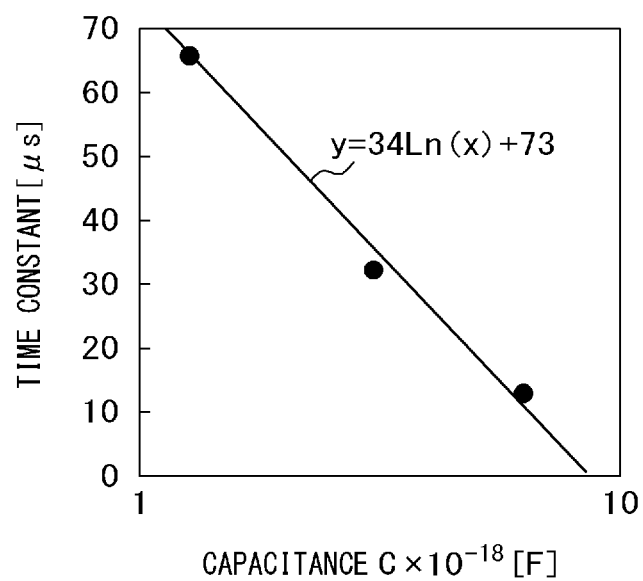
FIG. 3 is a drawing showing an example of calibration data (relation between the capacitance and time constant of an oxide film) used in an inspection method in the first embodiment of the present invention.
Figure 4:
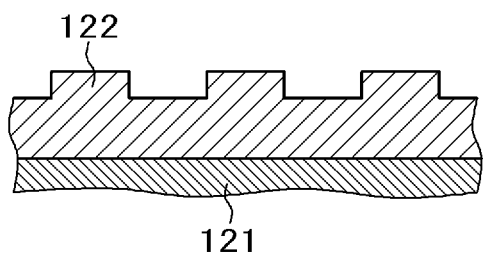
FIG. 4 is a drawing illustrating the cross-section structure of a sample used in the first embodiment.

FIG. 3 shows the relation between the capacitance of oxide films and time constant. In this embodiment, the relation between the capacitance of oxide films and time constant in FIG. 3 is taken as calibration data and the capacitance of a sample in an analysis position is extracted based on this calibration data. FIG. 4 is a block diagram of the section of a sample analyzed in this embodiment. In this sample, an oxide film 122 is formed over a substrate 121 and the length of the oxide film in the cross-sectional direction (depth direction) differs from region to region. In this embodiment, the length of each region in the cross-sectional direction (thickness of the oxide film) is analyzed.

Figure 5:
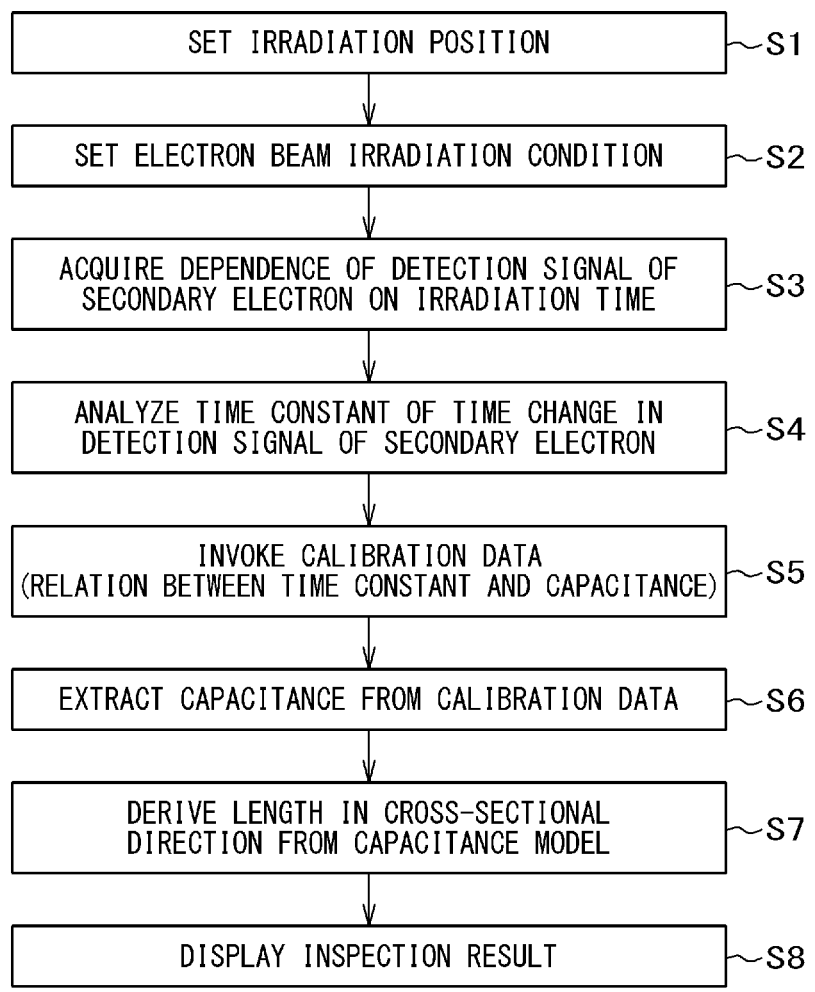
FIG. 5 is a drawing illustrating an example of an analysis flowchart included in an inspection method in the first embodiment of the present invention.

FIG. 5 is a flowchart for analyzing the length in the cross-sectional direction of a sample. In this embodiment, a sample having clearly known information in the cross-sectional direction is used beforehand to acquire the calibration data shown in FIG. 3, which is stored in a database. Referring to the database, the capacitance in the analysis position is extracted. The database can be stored in a storage portion provided in the control parameter setting unit, 118, the analysis and display unit 117, or the like; and the storage portion may be independently provided. How to acquire the calibration data is not limited to this embodiment and the calibration data may be acquired on an analysis-by-analysis basis. As shown in the flowchart in FIG. 5, an irradiation position of an electron beam for analyzing information in the cross-sectional direction (depth direction) is set (S1). Subsequently, electron beam irradiation conditions, such as acceleration voltage, irradiation current, and irradiation time, are set (S2). Setting at S1 and S2 is performed at the control parameter setting unit 118. In this embodiment, acceleration voltage is set to 300V, irradiation current is set to 10 pA, and irradiation time is set to 10 μs. Subsequently, the set position is irradiated with an electron beam to acquire the irradiation time dependence of a detection signal of secondary electrons (S3). Subsequently, from time change in the acquired detection signal of secondary electrons, the time constant with which the detection signal is brought into a steady state is analyzed (S4). The acquisition at S3 and the analysis at S4 are performed at the detection signal processing unit 115. Subsequently, the calibration data set in the database beforehand is invoked (S5). Subsequently, based on the calibration data, the capacitance of the irradiated area is extracted from the analyzed time constant (S6). Subsequently, using Equation (2), the length d in the cross-sectional direction (dimensions in the depth direction) is calculated (S7) and the result of the calculation is displayed in the analysis and display unit 117 (S8). The processing of S5 to S7 is carried out at the analysis and display unit 117.

Figure 6:
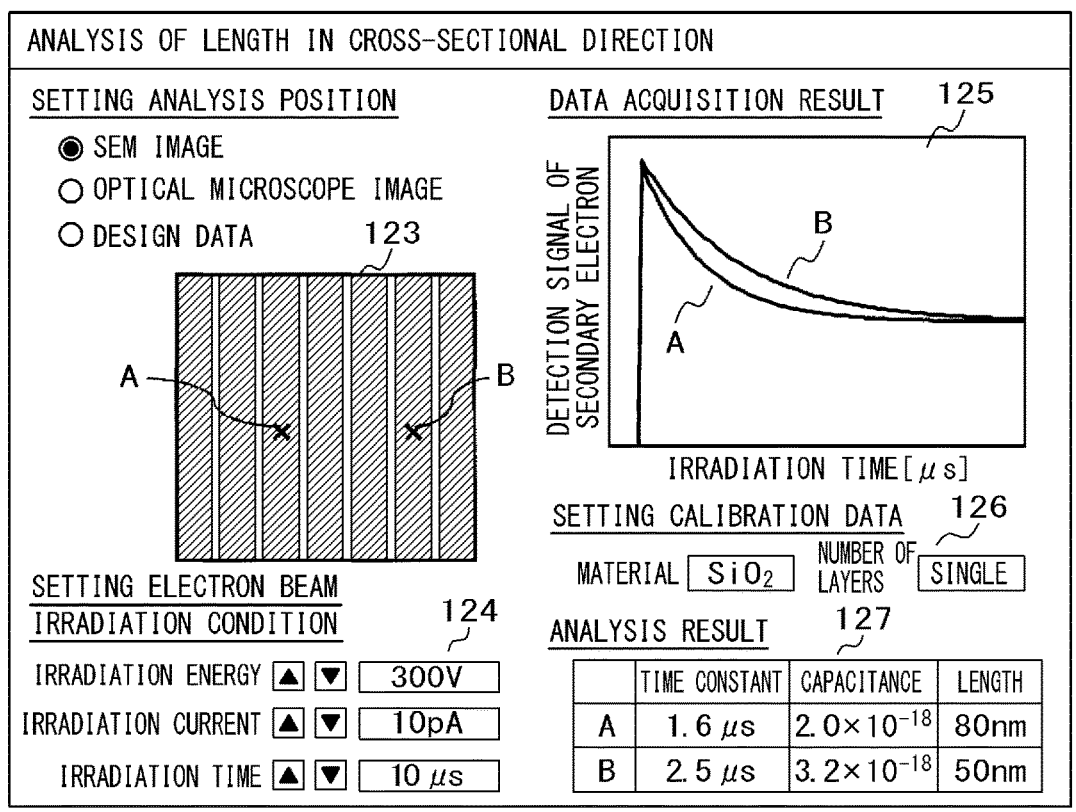
FIG. 6 is a drawing illustrating an example of GUI displayed in a display portion of a scanning electron microscope in the first embodiment of the present invention.

FIG. 6 illustrates an example of GUI displayed in the analysis and display unit 117. In a setting part 123 for irradiation position (analysis position), a position where the length in the cross-sectional direction is to be analyzed is determined. This determination is made based on a SEM image or an optical microscope image already picked up and design data generated when the sample is prepared. Electron beam irradiation conditions are set in an irradiation condition setting part 124. Irradiation energy may be set using a combination of the acceleration voltage of the electron beam and the voltage applied to the sample. The acquired irradiation time dependence of a detection signal of secondary electrons is displayed in an acquired data display part 125. This embodiment is provided with a calibration data setting part 126 for invoking previously acquired calibration data from the database. Time constant, capacitance, and length in the cross-sectional direction analyzed based on the irradiation time dependence of a detection signal of secondary electrons and calibration data are displayed in an analysis result display part 127.

As mentioned above, use of this embodiment makes it possible to provide a charged particle beam apparatus and an inspection method using the same. With the apparatus and inspection method, information in the cross-sectional direction (depth direction) of a sample having an internal structure can be acquired from the irradiation time dependence of a detection signal of secondary electrons in a nondestructive manner with reduced damage. Further, the electrical characteristics or cross-sectional morphological characteristics (depth of the internal structure and/or dimensions in the depth direction of the structure and the like) of the sample can be analyzed.

Second Embodiment

A description will be given to the second embodiment of the present invention with reference to FIG. 7 to FIG. 9. The items described in relation to the first embodiment and not found in the description of this embodiment can also be applied to this embodiment unless there are special circumstances. The description of this embodiment will be given to: the configuration of an electron microscope with enhanced accuracy of synchronization with a time base at the time of electron beam irradiation; and a method for analyzing the length in the cross-sectional direction (depth direction) of a sample made of a plurality of materials.

Figure 7:
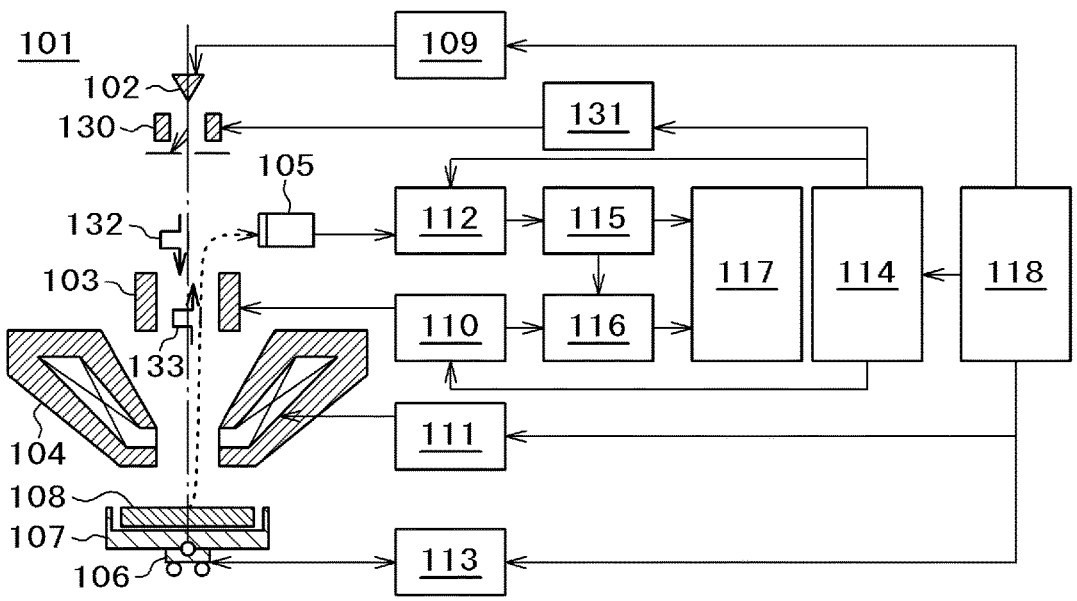
FIG. 7 is a block diagram illustrating an example of a charged particle beam apparatus (scanning electron microscope) in second to fourth embodiments of the present invention.

FIG. 7 is a block diagram of a scanning electron microscope in this embodiment. The scanning electron microscope in this embodiment is obtained by providing the scanning electron microscope illustrated in FIG. 1 with: a blanker 130 for interrupting an electron beam; and a blanking control unit 131 which applies a pulsed interruption control waveform to the blanker. The blanking control unit 131 applies a pulsed interruption control waveform to the blanker with timing controlled by the master clock generation unit 114. A pulsed electron beam 132 is applied to a sample by the blanker 130. Secondary electrons 133 pulsed and emitted from the sample are sampled by the detector control unit 112 with timing controlled by the master clock generation unit 114. This configuration makes it possible to control the amount of electron irradiation by adjusting the pulsed interruption control waveform applied to the blanker.

Figure 8:
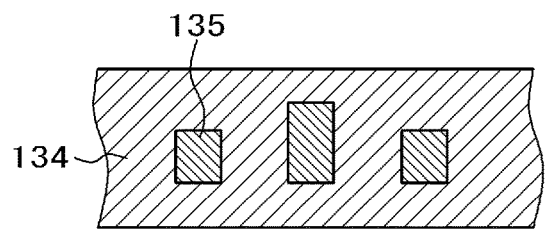
FIG. 8 is a drawing illustrating the cross-section structure of a sample used in the second embodiment of the present invention.
Figure 9:
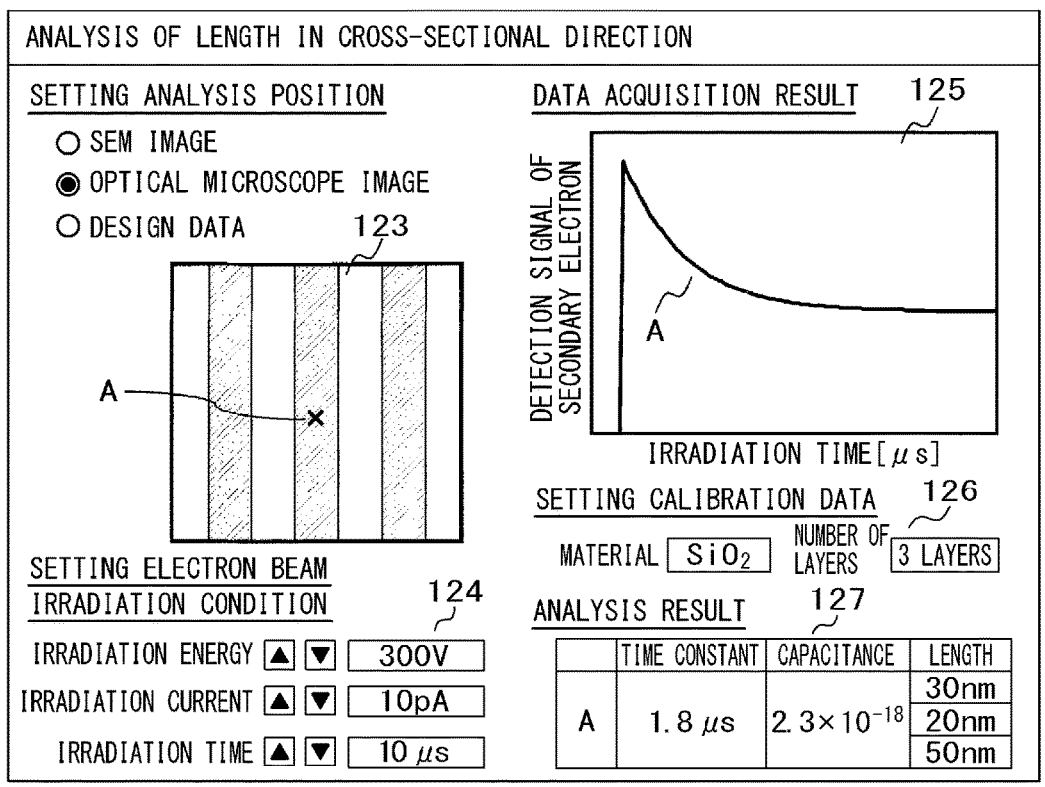
FIG. 9 is a drawing illustrating an example of GUI displayed in a display portion of a scanning electron microscope in the second embodiment of the present invention.

FIG. 8 a block diagram of a section of a sample used in this embodiment. The sample is an organic-inorganic hybrid material obtained by embedding resin 135 in silica 134. As illustrated in FIG. 8, a laminar structure of silica/resin/silica is formed in the cross-sectional direction; therefore, the model equation for capacitance is as expressed by Equation (5):

$$C = 1/C_1 + 1/C_2 + 1/C_3 \quad (5)$$

where, $C_1$, $C_2$, and $C_3$ respectively correspond to the laminar structure of silica/resin/silica. In this embodiment, the length in the cross-sectional direction of the embedded resin is analyzed. In this embodiment, the calibration data and analysis flowchart in the first embodiment are used. In this embodiment, the capacitance extracted using the calibration data is the synthetic capacitance of silica/resin/silica. It is known from the process for preparing the sample that the total thickness of the sample and the thickness of the base silica layer are equal to each other. With this condition taken into account, $C_1$, $C_2$, and $C_3$ were obtained using Equation (5) and the length in the cross-sectional direction was analyzed from each capacitance by Equation (3). FIG. 9 illustrates the GUI used in this embodiment. The capacitance extracted based on the calibration data and the lengths in the cross-sectional direction are displayed in an analysis result display part 127.

As mentioned above, use of this embodiment makes it possible to obtain the same effect as in the first embodiment. Even when an internal structure is made of a plurality of materials, the lengths in the cross-sectional direction can be analyzed from the irradiation time dependence of a detection signal of secondary electrons.

Third Embodiment

A description will be given to the third embodiment of the present invention with reference to FIG. 7 and FIG. 10 to FIG. 15. The items described in relation to the first or second embodiment and not found in the description of this embodiment can also be applied to this embodiment unless there are special circumstances. The description of this embodiment will be given to an electron microscope having a function of analyzing morphological characteristics in the cross-sectional direction (depth direction) using a SEM image to inspect an embedded pattern.

This embodiment uses the scanning electron microscope, illustrated in FIG. 7, capable of accurately controlling irradiation time by pulsing an electron beam. With this configuration, irradiation of the pulsed electron beam 132 and an irradiation position controlled by the deflector 103 are controlled with timing controlled by the master clock generation unit 114. Secondary electrons 133 pulsed and emitted from a sample are sampled by the detector control unit 112 with timing controlled by the master clock generation unit 114. A SEM image on the electron beam scanning plane is formed by the image formation unit 116. This image formation is performed based on the control waveform of the deflection signal control unit 110, the control waveform of the blanking control unit 131, and the value of the sampled detection signal of secondary electrons. In this embodiment, the amount of electron irradiation per unit area is controlled by the irradiation time width (hereafter, referred to as pulse width) of the pulsed electron beam. In this embodiment, the control waveform of the deflection signal control unit 110 is taken as a step signal, irradiation position is fixed on a pixel-by-pixel basis, and the amount of irradiation per unit pixel is controlled. Methods for controlling the amount of electron irradiation per unit area other than in this embodiment include: a method of controlling the amount of irradiation per unit scanning length by controlling the irradiation current or scanning speed of an electron beam; a method of controlling the amount of irradiation per unit scanning length by controlling a pulse width and time intervals between pulses in synchronization with scanning; and a method of controlling the amount of irradiation per unit visual field by controlling the number of repetitions by which an identical region is repeatedly irradiated. Any method can be used as a method for controlling the amount of electron irradiation.

Figure 10:
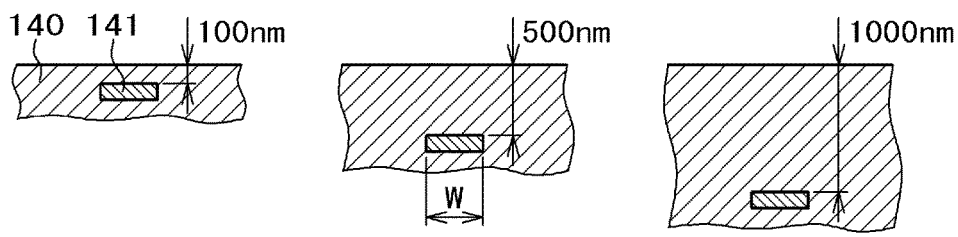
FIG. 10 is a drawing illustrating the cross-section structures of samples used in the third embodiment of the present invention.

FIG. 10 is a block diagram of sample sections having three different embedding depths analyzed in this embodiment. The samples are formed by embedding a line pattern (wiring pattern) 141 of polysilicon in an oxide film 140. The line pattern 141 of polysilicon is embedded in positions at 100 nm, 500 nm, and 1000 nm from the surface of the oxide film 140. In this embodiment, the line patterns 141 of polysilicon are grounded. As the result of grounding the line patterns 141, the sensitivity of embedding depth inspection is enhanced. In case the line patterns 141 of polysilicon are not grounded, the capacitance is synthetic capacitance to the sample holder (ground) on the underside of the sample; therefore, it is possible to inspect the thickness of each line pattern 141 of polysilicon and the thickness below the line pattern. It is desirable that whether to ground a conductor portion or not should be taken into account according to inspection items.

Figure 11:
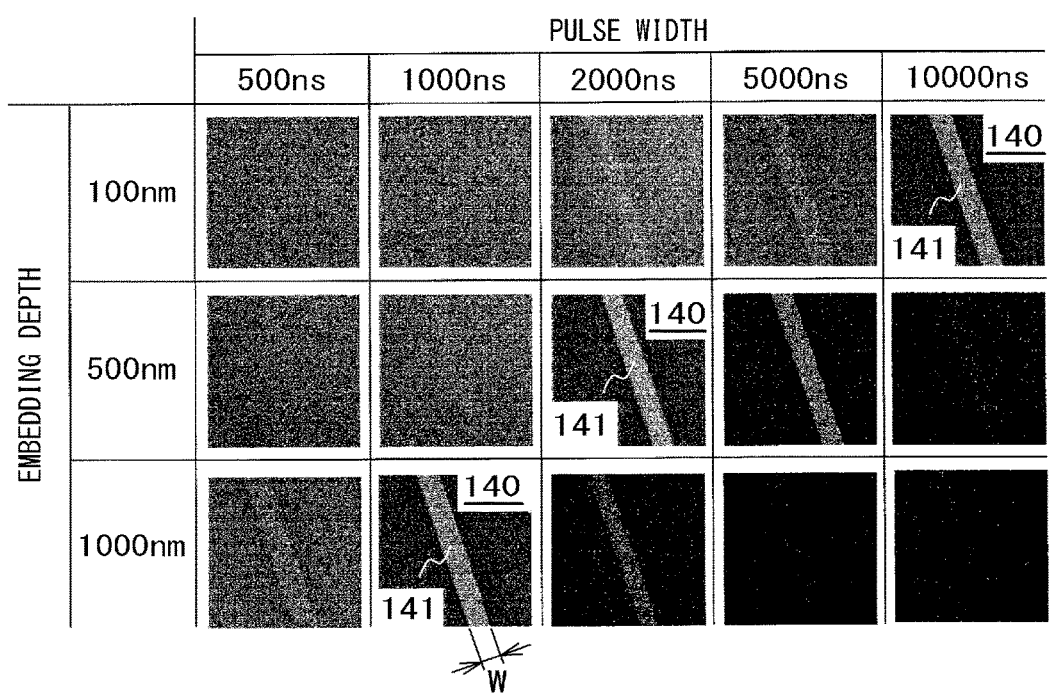
FIG. 11 is a plan view illustrating examples of SEM images picked up by applying an electron beam to samples under the condition of different pulse widths in a scanning electron microscope in the third embodiment of the present invention.

FIG. 11 shows SEM images (plan views) of samples having three different embedding depths picked up with acceleration voltage of 300V and irradiation current of 10 pA. The pulse width was controlled in the range of 500 ns to 10000 ns. In any of the samples having three different embedding depths (100 nm, 500 nm, 1000 nm), the viewability of the line patterns 141 of polysilicon is enhanced with increase in pulse width. After the contrast is maximized, the brightness of entire images is reduced and the viewability of the line patterns 141 of polysilicon is degraded. It is understood that the pulse width with which the contrast is maximized is shortened with increase in the embedding depth of the line patterns 141 of polysilicon. The contrast is expressed by Equation (4). In this embodiment, the surface is an oxide film and thus the true secondary electron emission rates $\sigma_{iA}$, $\sigma_{iB}$ not influenced by electrification exhibit an identical value regardless of whether the region is A or B. Therefore, as represented by Equation (4), the contrast of the embedded lower layer pattern depends only on the difference in time constant in regions A and B and thus the contrast Is maximized by control of irradiation time t (pulse width). Since the difference in time constant in regions A and B is a difference in capacitance of samples, the pulse width with which the contrast is maximized differs in a sample different in embedding depth (different in capacitance). In this embodiment, a characteristic that the pulse width with which the contrast is maximized depends on capacitance is used to analyze the cross-sectional morphological characteristics of an embedded pattern.

Figure 12:
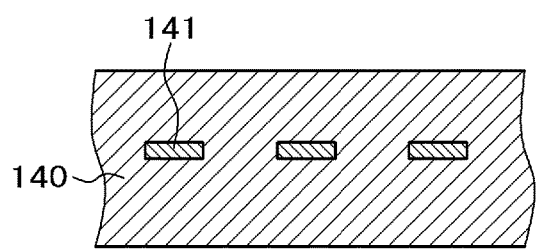
FIG. 12 is a drawing illustrating the cross-section structure of a different sample used in the third embodiment of the present invention.

FIG. 12 is a block diagram of a section of a sample used in this embodiment and in this sample, a metal wiring pattern 141 is embedded in an oxide film. This sample is a wafer sample in a manufacturing process for semiconductor devices. In this embodiment, any morphological variation in the cross-sectional direction in a wafer plane is inspected.

Figure 13:
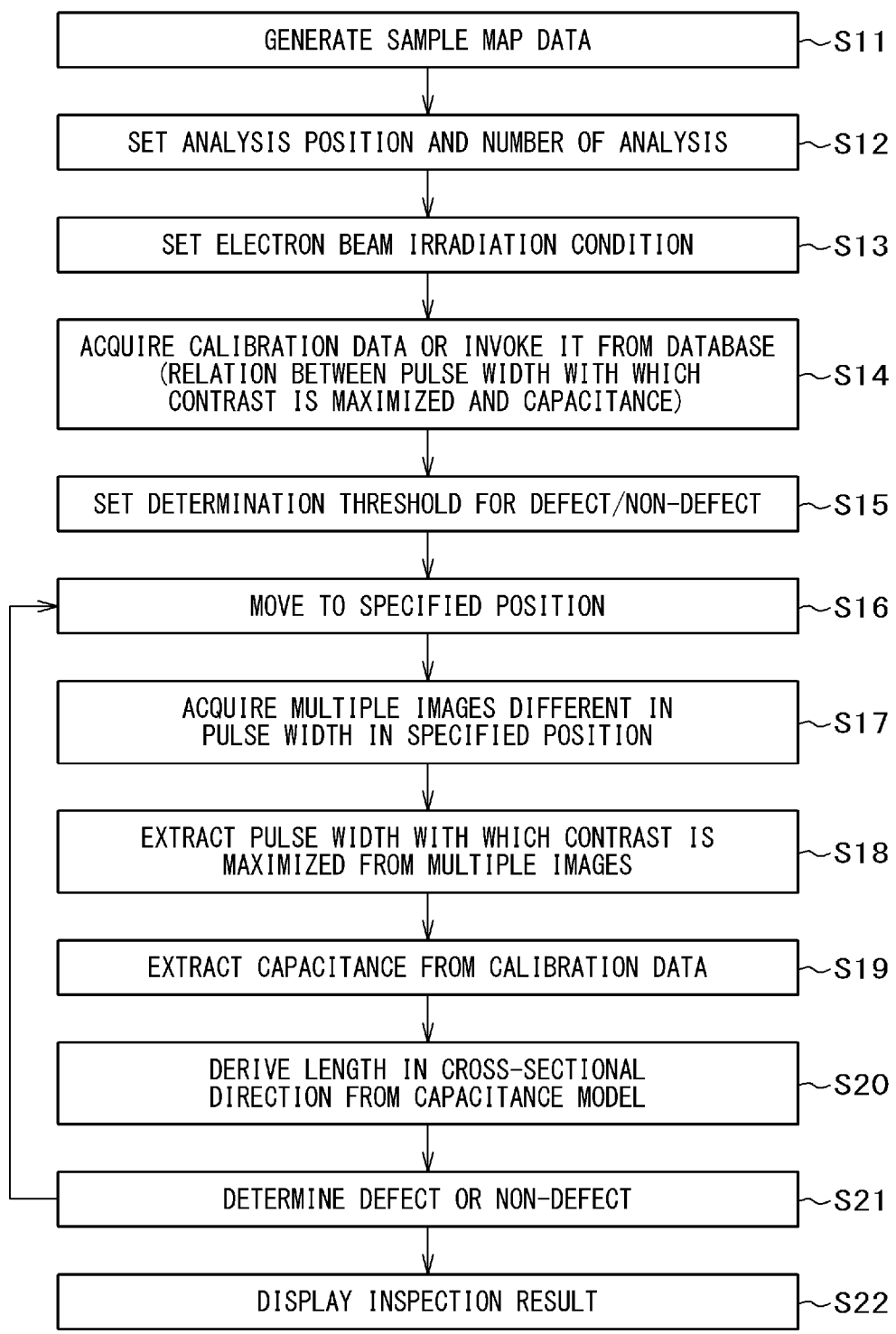
FIG. 13 is a drawing illustrating an example of an analysis flowchart included in an inspection method in the third embodiment of the present invention.

FIG. 13 shows an inspection flowchart for inspecting any morphological variation in the cross-sectional direction in a wafer plane. First, a map data of the wafer is generated (S11). At this step, a map of the wafer is set on the basis of each chip of the semiconductor device. (Die will be hereafter taken as this unit of chip.) The dies are arranged in an identical repetitive pattern. Subsequently, an analysis position in a die and a die to be analyzed are set (S12). Electron beam irradiation conditions, such as acceleration voltage, irradiation current, and irradiation time, are set (S13). The processing of S11 to S13 is performed at the control parameter setting unit 118. In this embodiment, acceleration voltage is set to 300V, irradiation current is set to 5 pA, and pulse width is controlled from 1000 ns to 10000 ns in increments of 1000 ns. The value of pulse width with which the contrast is maximized is extracted from 10 images, different in pulse width, in total.

FIG. 14 shows the relation between capacitance and a value of pulse width with which the contrast is maximized, acquired using samples with clearly known capacitance. In this embodiment, the calibration data in FIG. 14 is stored beforehand as a database and is invoked from the database and used during inspection (S14). The processing of S14 is performed by the analysis and display unit 117. Subsequently, a criterion for whether a sample is defective or non-defective is established (S15). The processing of S15 is performed at the control parameter setting unit. In this embodiment, the breadth of an embedded wiring and the depth position in the cross-sectional direction of the wiring are inspected. In this embodiment, threshold values for breadth and depth position are established based on design data of the device. With respect to the threshold values in this embodiment, the breadth is set to ±5 nm and the depth position is set to ±10 nm. Another method for establishing threshold values is to analyze breadth and depth position in a plurality of arbitrary places and determine threshold values from a histogram of the analysis result.

Subsequently, the electron beam is moved to the analysis position set at Step S12 (S16) and a plurality of SEM images are acquired under a plurality of pulse width conditions (S17). The processing of S16 is performed at the XYZ stage control unit 113 and the processing of S17 is performed at the image formation unit 116. In this embodiment, the pulse width is controlled from 1000 ns to 10000 ns in increments of 1000 ns and 10 SEM images in total are acquired. The contrasts of the SEM images are analyzed and the value of pulse width with which the contrast is maximized is extracted (S18). In this embodiment, Equation (6) below is used to analyze contrast CNR:

$$CNR=(S_A-S_B)/(\delta_A-\delta_B) \qquad (6)$$

where, $S_A$ and $S_B$ are image brightness in a region without a wiring underneath and a region with a wiring underneath; and $\delta_A$ and $\delta_B$ are the standard deviation of image brightness of the region without a wiring underneath and the region with a wiring underneath. The capacitance of the region with a wiring underneath is extracted from the calibration data in FIG. 14 based on the value of pulse width with which the contrast is maximized, analyzed at Step S18 (S19). In this embodiment, the wiring portion is a conductor; therefore, the single layer model of Equation (3) is used to derive the depth position of the wiring (S20). Based on the non-defective/defective criterion established at Step S15, it is determined whether the analyzed portion is non-defective or defective (S21). The processing of S18 to S21 is performed at the analysis and display unit 117.

Figure 15:
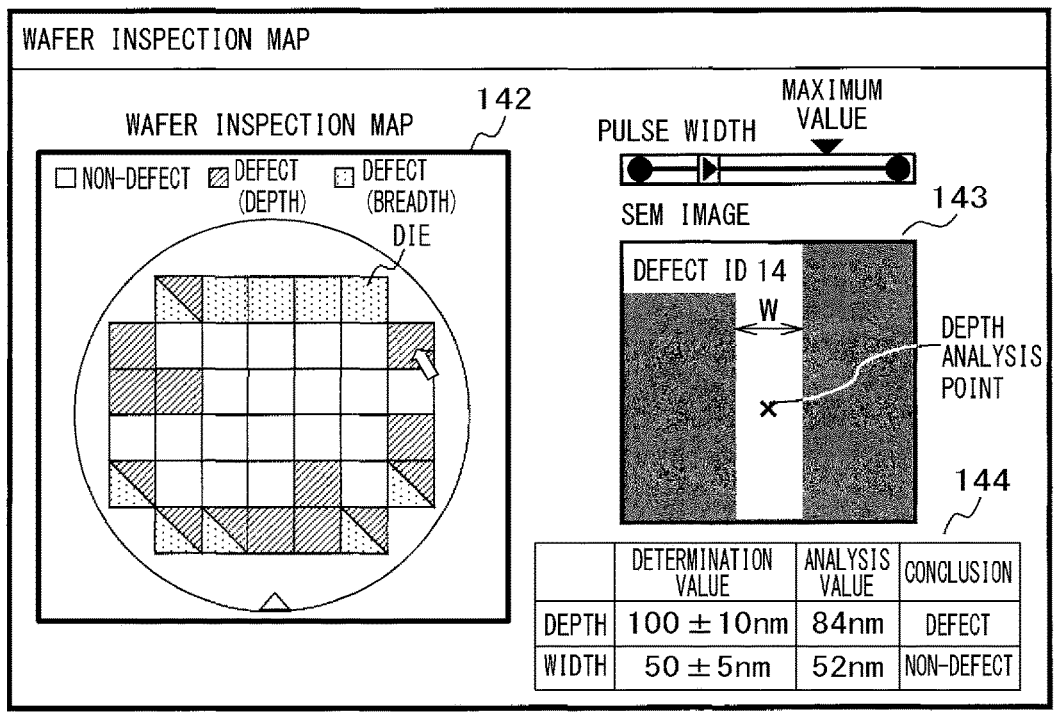
FIG. 15 is a drawing illustrating an example of GUI displayed in a display portion of a scanning electron microscope in the third embodiment of the present invention.

Subsequently, the electron beam is moved to another analysis position in the die or an analysis position in another die determined at Step S12. Then the processing of Step S16 to Step S21 is repeated and after the completion of the inspection, the result is displayed in the analysis and display unit 117 (S22). FIG. 15 illustrates GUI for displaying inspection results. The GUI is composed of: an inspection map display part 142 for displaying an inspection map based on the set design of the wafer; a SEM image display part 143 for displaying an inspection SEM image of a die (for example, defect ID 14, indicated by an arrow) selected by the inspection map display part 142; and an inspection result display part 144 for indicating the result of inspection of the wiring of the die.

As mentioned above, use of this embodiment makes it possible to obtain the same effect as in the first embodiment. Further, depth positions in the cross-sectional direction can also be inspected from a plurality of SEM images different in pulse width.

Fourth Embodiment

A description will be given to the fourth embodiment of the present invention with reference to FIG. 7 and FIG. 16 to FIG. 19. The items described in relation to any of the first to third embodiments and not found in the description of this embodiment can also be applied to this embodiment unless there are special circumstances. The description of this embodiment will be given to an electron microscope having a function of analyzing morphological characteristics in the cross-sectional direction (depth direction) using a SEM image to inspect an embedded pattern.

Figure 16:
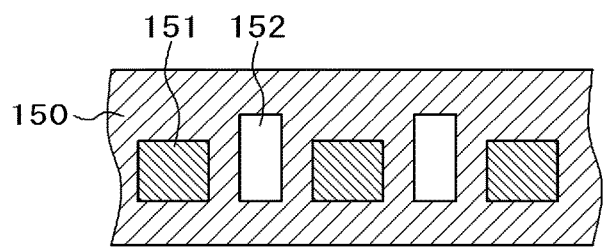
FIG. 16 is a drawing illustrating the cross-section structure of a sample used in the fourth embodiment of the present invention.

This embodiment uses the scanning electron microscope, illustrated in FIG. 7, capable of accurately controlling irradiation time by pulsing an electron beam. FIG. 16 is a sectional view of a sample analyzed in this embodiment. Wirings 151 are embedded in an insulating film 150 low in permittivity and air gaps 152 with relative permittivity of 1 are formed between wirings. This sample is a wafer sample in the process of manufacture of a semiconductor device; and in this embodiment, the length in the cross-sectional direction (dimension in the depth direction) of an air gap in a wafer plane is analyzed and inspected. In the third embodiment, a plurality of SEM images different in pulse width are acquired at set analysis points and a pulse width with which the contrast is maximized is calculated from the SEM images. In this embodiment, a defective part is determined from a SEM image acquired under a single pulse width condition and the length in the cross-sectional direction of the extracted defective air gap is analyzed. When images are picked up with a pulse width of 2000 ns, as shown in FIG. 11, as compared with the SEM image with an embedding depth of 500 nm, the contrast is reduced and the entire image becomes brighter with increase in capacitance (embedding depth of 100 nm). As compared with the SEM image with an embedding depth of 500 nm, the contrast is reduced and the entire image becomes darker with decrease in capacitance (embedding depth of 1000 nm). That is, by acquiring a SEM image under a pulse width condition under which contrast is obtained at a reference capacitance, a defect can be determined from the brightness and contrast of the SEM image.

Figure 17:
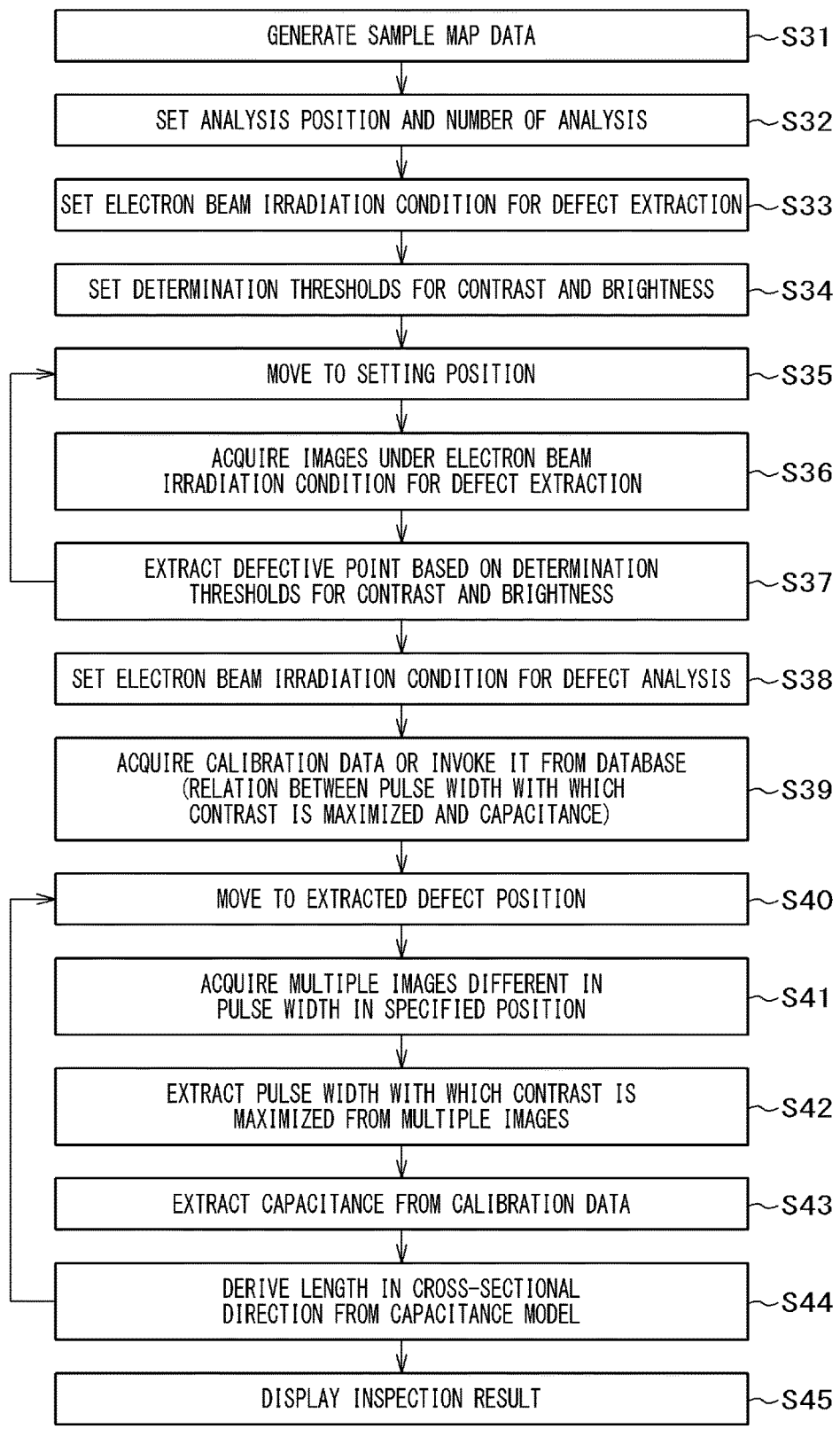
FIG. 17 is a drawing illustrating an example of an analysis flowchart included in an inspection method in the fourth embodiment of the present invention.

FIG. 17 is an inspection flowchart for inspecting the length (dimension in the depth direction) of an air gap in this embodiment. The processing of Step S31 to Step 37 is for determining any defect and the processing of Step S38 to Step S45 is for analyzing the length in the cross-sectional direction of the extracted defective air gap.

First, map data of the wafer is generated (S31). Subsequently, an analysis position in a die set in the map data and a die to be analyzed are set (S32). In addition, electron beam irradiation conditions, such as acceleration voltage, irradiation current, and pulse width, are set (S33). In this embodiment, acceleration voltage is set to 300V; irradiation current is set to 5 pA; and pulse width is set to 2000 ns. Subsequently, determination threshold values of the contrast and brightness of a SEM image are set as defect/non-defect criteria (S34). In this embodiment, threshold values are established from a histogram of the contrast and brightness of SEM images extracted on a random basis when an inspection recipe is created. The processing of S31 to S34 is performed at the control parameter setting unit 118.

Subsequently, the electron beam is moved to the analysis position set at Step S32 (S35); a SEM image is acquired under the electron beam conditions set at Step S33 (S36); and the contrast and brightness of the SEM image are analyzed and a defective point is extracted based on the criteria set at Step S34 (S37). The processing of S35 is performed at the XYZ stage control unit 113; the processing of S36 is performed at the image formation unit 116; and the processing of S37 is performed at the analysis and display unit 117.

Subsequently, the electron beam is moved to another analysis position in the die or an analysis position in another die set at Step S32 and the processing of Step S35 to Step 37 is repeated. In this embodiment, after a defective point is extracted, the defect is analyzed in detail. However, detailed defect analysis is not necessarily required and the flow may be terminated at Step 37.

Subsequently, irradiation conditions are set for an electron beam having a plurality of pulse widths for defect analysis (S38). In this embodiment, acceleration voltage is set to 300V; irradiation current is set to 5 pA; and pulse width is controlled from 500 ns to 10000 ns in increments of 500 ns. For calibration data, the calibration data in FIG. 14 is held beforehand as a database and is invoked from the database and used during inspection (S39). The processing of S38 is performed at the control parameter setting unit 118 and the processing of S39 is performed at the analysis and display unit 117.

Subsequently, the electron beam is moved to the defective point (coordinates) extracted at Step 37 (S40) and a plurality of SEM images, different in pulse width, are acquired (S41). The processing of S40 is performed at the XYZ stage control unit and the processing of S41 is performed at the image formation unit 116. Subsequently, the contrast of the SEM images is analyzed and a value of pulse width with which contrast is maximized is extracted (S42). Subsequently, based on the pulse width value with which contrast is maximized, analyzed at Step S42, the capacitance of a region embracing an air gap is extracted from the calibration data in FIG. 14 (S43). In this embodiment, the air gaps 152 are placed in the insulating film 150 low in permittivity; therefore, the lamination model of Equation (5) is used to derive the length in the cross-sectional direction of each air gap (S44). The processing of S42 to S44 is performed at the analysis and display unit 117. Subsequently, the electron beam is moved to the defective point (coordinates) extracted at Step S37 and the processing of Step S41 to Step S44 is repeated. After the completion of inspection, the result is displayed in the analysis and display unit 117 (S45).

Figure 18:
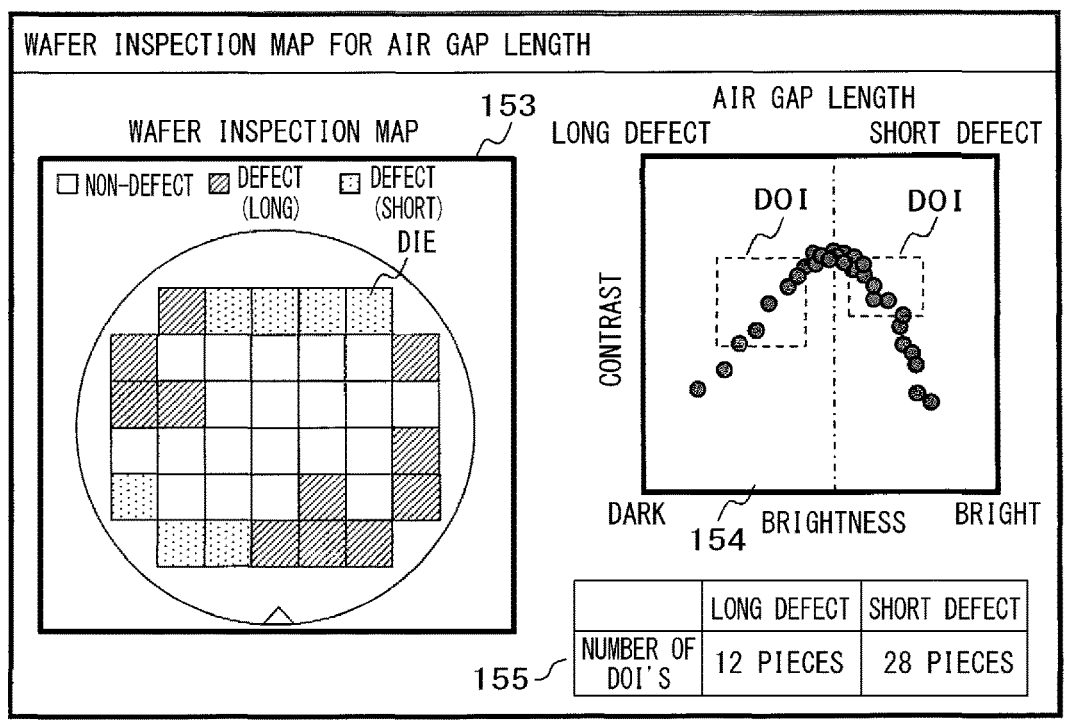
FIG. 18 is drawing illustrating an example of GUI displayed in a display portion of a scanning electron microscope in the fourth embodiment of the present invention.
Figure 19:
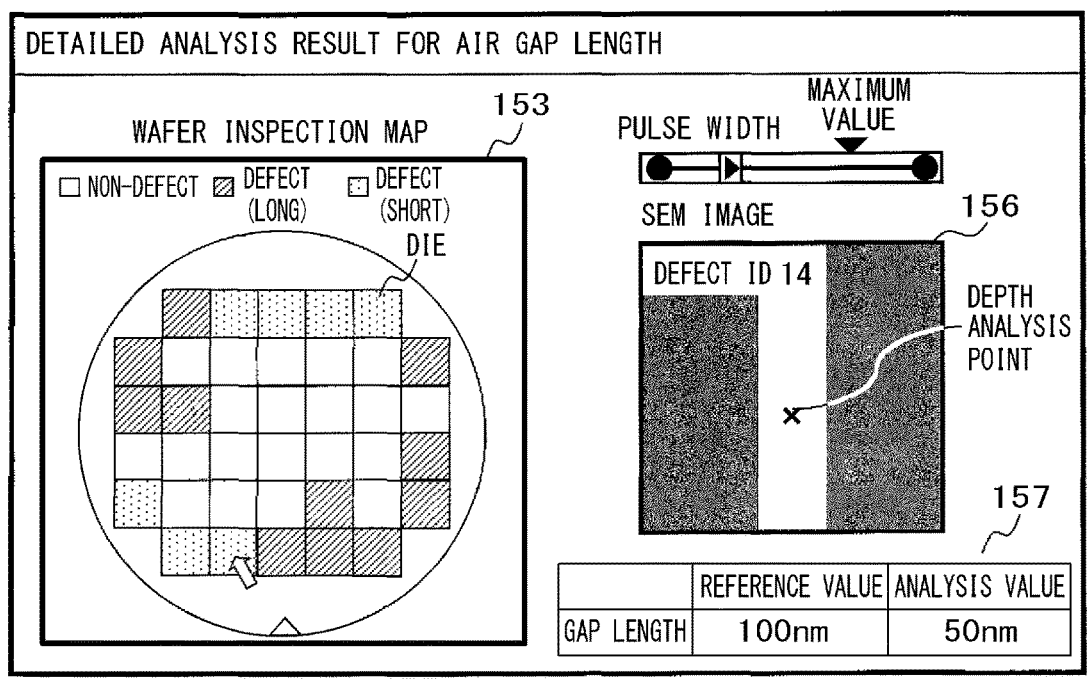
FIG. 19 is a drawing illustrating another example of GUI displayed in a display portion of a scanning electron microscope in the fourth embodiment of the present invention.

FIG. 18 and FIG. 19 illustrate the GUIs used in this embodiment. The GUI in FIG. 18 is for displaying the result of defective point extraction; and the GUI in FIG. 19 is for displaying the result of analyzing the length in the cross-sectional direction (dimension in the depth direction) of the defective air gap extracted in FIG. 18.

As illustrated in FIG. 18, an inspection map display part 153 displays a die including a defective air gap and the features (longer or shorter than a reference length) of the defective air gap. A SEM image analysis display part 154 displays a distribution map of the contrast and brightness of a SEM image. With respect to air gaps, the capacitance is increased with decrease in the length in the cross-sectional direction of the air gap and thus the brightness of a SEM image is increased. Meanwhile, with increase in the length in the cross-sectional direction of the air gap, the capacitance is reduced and the brightness is reduced. The SEM image analysis display part 154 determines whether an air gap is long or short with this characteristic taken into account. The display part also displays the threshold values for defect extraction described in relation to Step S34. In the description of this embodiment, a defect extracted based on the threshold values is designated as DOI. An inspection result display part 155 displays numbers of air gap defects as the result of inspection.

FIG. 19 illustrates the result of analyzing the length in the cross-sectional direction (dimension in the depth direction) of the air gap extracted as DOI. A SEM image display part 156 displays SEM images picked up with a plurality of pulse widths of DOI managed by ID; and a detailed analysis result display part 157 displays the result of analysis of air gap length. The arrow at the lower left of the wafer inspection map indicates a die with defect ID of 14.

As mentioned above, use of this embodiment makes it possible to obtain the same effect as in the first embodiment.

Further, it is possible to identify defective points different in shape in the cross-sectional direction from a SEM image and analyze the length in the cross-sectional direction (dimension in the depth direction) of the defect.

The present invention is not limited to the above-mentioned embodiments and includes various modifications. The above detailed description of the embodiments is intended to make it easier to understand the present invention; and the present invention is not limited to embodiments including all the above-mentioned constitutional elements. A part of the configuration of some embodiment may be substituted for the configuration of another embodiment; and the configuration of some embodiment may be added to the configuration of another embodiment. The configuration of each embodiment may be added to, deleted from, or substituted for a part of the configuration of another embodiment.

What is claimed is:

1. A charged particle beam apparatus comprising:
   a charged particle beam source;
   a control parameter setting portion of a Scanning Electron Microscope (SEM) control system configured to set irradiation energy of a charged particle beam emitted from the charged particle source;
   a master clock generator configured to provide a time base for a control signal;
   a deflection signal controller configured to apply the charged particle beam to a sample in synchronization with the time base and to control an irradiation position;
   a detection controller configured to detect an emission electron from the sample received by a detector in synchronization with the time base;
   a detection signal processor configure to analyze emission characteristics of the emission electron from a detection signal of the emission electron; and
   an analysis and display portion of the SEM control system configured to analyze electrical characteristics or cross-sectional morphological characteristics of the sample based on the emission characteristics of the emission electron.

2. The charged particle beam apparatus according to claim 1,
   wherein the emission characteristics of the emission electron is a signal value of a detection signal of the emission electron, a time constant at which a detection signal of the emission electron is brought into a steady state, or an integrated value obtained by integrating a detection signal of an emission electron by time.

3. A charged particle beam apparatus comprising:
   a charged particle beam source;
   a control parameter setting portion of a Scanning Electron Microscope (SEM) control system configured to set irradiation energy of a charged particle beam emitted from the charged particle source;
   a master clock generator configured to provide a time base for a control signal;
   a deflection signal controller configured to apply the charged particle beam to a sample in synchronization with the time base and to control an irradiation position;
   a detection controller configured to detect an emission electron from the sample in synchronization with the time base;
   an image formation portion of the SEM control system configured to form an image from a first control signal for controlling the irradiation position, a second control signal for applying the charged particle beam to the sample, and a detection signal of the emission electron; and
   an analysis and display portion of the SEM control system configured to analyze the electrical characteristics or cross-sectional morphological characteristics of the sample from the brightness or contrast of the image.

4. The charged particle beam apparatus according to claim 3,
   wherein the analysis and display portion uses a plurality of images acquired under a plurality of irradiation conditions for analyzing the electrical characteristics or cross-sectional morphological characteristics of the sample.

5. The charged particle beam apparatus according to claim 1,
   wherein the deflection signal controller intermittently applies the charged particle beam in synchronization with the time base for applying the charged particle beam to the sample in synchronization with the time base.

6. The charged particle beam apparatus according to claim 5,
   wherein the irradiation condition for intermittent irradiation is an irradiation time and time intervals between irradiations.

7. The charged particle beam apparatus according to claim 1,
   wherein the electrical characteristics of the sample are a value of the capacitance or resistance of the sample, and
   wherein the cross-sectional morphological characteristics are the depth position, length, and thickness in the cross-sectional direction of a structure.

8. The charged particle beam apparatus according to claim 1,
   wherein the analysis and display portion which analyzes the electrical characteristics or cross-sectional morphological characteristics of the sample includes a database indicating the relation between the emission characteristics of the emission electron and the electrical characteristics or cross-sectional morphological characteristics or the relation between the brightness or contrast of the image and the electrical characteristics or cross-sectional morphological characteristics, and
   wherein the analysis and display portion analyzes the electrical characteristics or cross-sectional morphological characteristics of the sample from a detection signal of the emission electron or the image based on each relation stored in the database.

9. The charged particle beam apparatus according to claim 3,
   wherein the analysis and display portion which analyzes the electrical characteristics or cross-sectional morphological characteristics of the sample analyzes the electrical characteristics or the cross-sectional morphological characteristics in a plurality of places in the sample and displays the electrical characteristics or the cross-sectional morphological characteristics mapped.

10. The charged particle beam apparatus according to claim 3,
    wherein the sample is a wafer in the process of manufacture of a semiconductor device, and
    wherein the analysis and display portion which analyzes the electrical characteristics or cross-sectional morphological characteristics of the sample is further configured to analyze the dimensions of a fine pattern formed in the wafer or any malformation of the fine pattern from the image.

11. The charged particle beam apparatus according to claim 10,
wherein the analysis and display portion which analyzes the dimensions of a fine pattern formed in the wafer or any malformation of the fine pattern from the image is further configured to extract a defective point in a fine pattern formed in the wafer from a difference in brightness or contrast of images acquired under the single irradiation condition and to analyze the electrical characteristics or cross-sectional morphological characteristics of the sample based on the brightness or contrast of a plurality of images analyzed from the images acquired at the extracted defective point under a plurality of irradiation conditions.

12. An inspection method comprising the steps of:
preparing a test sample in which a conductive layer is covered with an insulating layer;
applying charged particle beams different in pulse width to a region of interest in the test sample with the conductive layer formed through the insulating layer to acquire a plurality of images different in contrast;
extracting a pulse width with which contrast is maximized from the images;
using the relation between pulse width with which contrast is maximized and capacitance, obtained using a standard sample in which the thickness of an insulating layer so formed as to cover a conductive layer is known to extract capacitance corresponding to a pulse width with which contrast is maximized in the region of interest in the test sample;
using the extracted capacitance to determine the depth position of the conductive layer in the test sample; and
comparing the determined depth position of the conductive layer with a predetermined criterion to determine whether the test sample is non-defective or defective.

13. The inspection method according to claim 12, wherein the conductive layer in the test sample is grounded.

* * * * *